Figure 1:
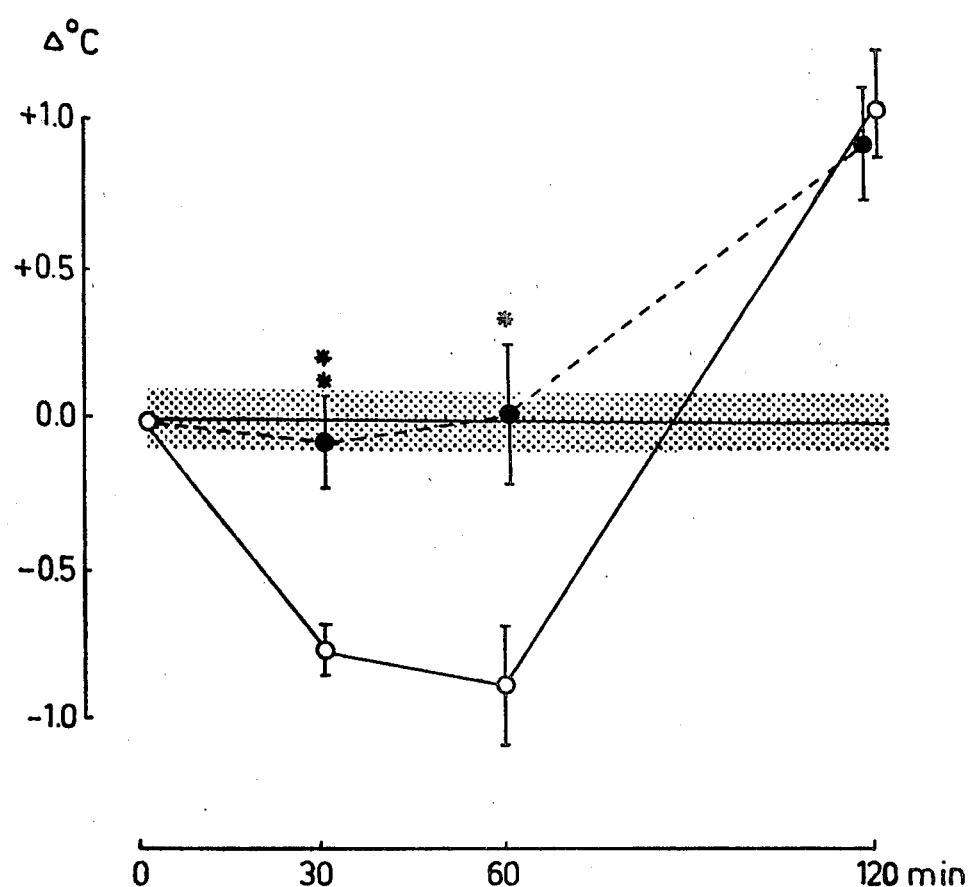

United States Patent [19]

de Wied et al.

[11] 4,410,511

[45] Oct. 18, 1983

[54] BIOLOGICALLY ACTIVE PEPTIDES

[75] Inventors: David de Wied, Bilthoven; Hendrik M. Greven, Heesch, both of Netherlands

[73] Assignee: Akzo N.V., Arnhem, Netherlands

[21] Appl. No.: 275,049

[22] Filed: Jun. 18, 1981

[30] Foreign Application Priority Data

Jun. 25, 1980 [DE] Fed. Rep. of Germany ....... 3023813

[51] Int. Cl.$^3$ ............................................ H61K 37/00
[52] U.S. Cl. .................................................... 424/177
[58] Field of Search ........................................ 424/177

[56] References Cited

PUBLICATIONS

Chem. Abstr. 92, (1980), 71322s.
Chem. Abstr. 95, (1981), 183336t.
Chem. Abstr. 95, (1981), 199395x.
Chemical & Pharmaceutical Bulletin 28, No. 9, (1980), 2839–2843.
Journal Canadien de Biochimie 54, No. 6, (1976), 566–569.
N. Ling et al., Life Science, vol. 25, pp. 1773–1780, (1979).

*Primary Examiner*—Delbert R. Phillips
*Attorney, Agent, or Firm*—Abelman, Frayne & Rezac

[57] ABSTRACT

The present invention is dealing with a pharmaceutical composition containing a peptide of the formula:

$R_1$-L-Tyr-L-Val-L-Met-Gly-L-His-L-Phe-L-Arg-L-Trp-L-Asp-L-Arg-L-Phe-$R_2$     I in which
  $R_1$ represents hydrogen or a lower aliphatic acyl (1–6 C) group and
  $R_2$ represents the group —OH or —Gly—OH,
as well as salts, esters and amides thereof.

5 Claims, 2 Drawing Figures

BIOLOGICALLY ACTIVE PEPTIDES

It has been found some time ago, that the pituitary hormones corticotrophin (ACTH) and β-lipotropin (β-LPH) are derived from a large common precursor protein. The proposed primary structure of this precursor molecule contains several pairs of basic amino acid residues which may be attacked by proteolytic enzymes yielding various smaller peptides. In this way ACTH and β-LPH and subsequently i.a. α-MSH, γ-LPH, β-MSH and β-endorphin can be formed. Outside the sequence of ACTH and β-LPH in said precursor molecule, a fragment is present with an amino acid sequence which is strikingly similar to that of α-MSH and β-MSH. In view of this structural relationship, that portion of the precursor molecule was called γ-MSH.

Ling et al, Life Science 25, 1773 (1979), synthesized this hypothetical hormone, γ-MSH, and also some closely related derivatives thereof. They found that none of these peptides possess significant MSH activity (compared with α-MSH), and that these peptides do not stimulate in vitro the release of other hormones, such as luteinizing hormone, follicle stimulating hormone, prolactin, growth hormone and thyroid stimulating hormone.

In view of its close structural similarity with ACTH/MSH type of peptides, which have been shown to affect also certain brain functions, γ-MSH was examined in those behavioral procedures in which ACTH/MSH related neuropeptides have been found effective. The new peptide and its derivatives did not show similar effects in these testsystems.

Surprisingly, however, it appeared that γ-MSH derivatives of the general formula:

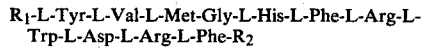

R$_1$-L-Tyr-L-Val-L-Met-Gly-L-His-L-Phe-L-Arg-L-Trp-L-Asp-L-Arg-L-Phe-R$_2$     I in which
  R$_1$ represents hydrogen or a lower aliphatic acyl (1–6 C) group and
  R$_2$ represents the group —OH or —Gly—OH,
as well as salts, esters and amides thereof, induce behavioral changes just opposite to those found with for example α-MSH, ACTH (1–24) and β-endorphin.

It is well known that α-MSH, β-endorphin and ACTH fragments such as ACTH (1–24), ACTH (1–10) and ACTH (4–10), affect avoidance behavior as can be shown in the so-called pole-jumping and shuttle box tests. Said peptides delay significantly the extinction of pole-jumping behavior while, in contrast, γ-endorphin, certain chemically modified ACTH fragments and also well known opiate antagonists such as naloxone and naltrexone, induce an opposite effect, viz. a facilitation of the extinction of pole-jumping avoidance behavior. The peptides of formula I facilitate extinction of avoidance response as well.

Another avoidance behavior influenced by ACTH (1–24) is the acquisition of shuttle box avoidance behavior. Using this test procedure it was observed that subcutaneous injection of a peptide of the invention decreased significantly the rate at which rats acquired the avoidance response. In this respect the test results obtained with the present peptides run paralel with those obtained with the opiate antagonist naloxone.

ACTH (1–24) and some related peptides are further known to induce an excessive grooming response in rats when injected intracerebroventricularly (icv). α-MSH, β-MSH and ACTH (1–24) are about equally potent in this respect while the peptides of the invention turned out to be virtually inactive. However, after subcutaneous treatment with a peptide of formula I, ACTH (1–24) induced excessive grooming was clearly attenuated. Since it has been suggested that this grooming behavior is mediated by an opiate-sensitive system, the peptides of formula I might also exert their suppressive action by interfering with an opiate-sensitive system.

β-Endorphin induced hypothermia at ½ and 1 hour after injection was attenuated in rats, which had received a previous icv injection with a peptide according to formula I, viz. 50 μg of γ-MSH.

This β-endorphin antagonizing activity was further shown in a study following chronic treatment with β-endorphin and γ-MSH.

Apart from the development of tolerance and physical dependence, the most striking effect of β-endorphin in this respect is the drug-seeking behavior, which can be analyzed reliably in self administration experiments.

β-Endorphin, as many narcotic drugs like heroin do, induces in rats a self administration behavior. Although γ-MSH did not immediately interfere with this self administration behavior, on day 5 of testing a dose-dependent suppression of this behaviour could be demonstrated.

The above test results in animal experiments clearly suggest the present peptides to be active as β-endorphin antagonists, which means that they counteract the effects of the well known endogenous neuropeptide β-endorphin.

In addition, the peptides are active in antagonizing and counteracting the effects of those enkephalins and endorphins which act upon the opiate receptors in the brain, so that they can antagonize the effects of the opiate like endogenous peptides. In this context the present peptides have a pharmacological action that resembles that of the classic narcotic antagonists, such as naloxone or naltrexone, in many respects, which means that they may be used for example in antagonizing narcotic analgesia and more particularly in reversing narcotic induced respiratory depression.

In veiw of the results in the avoidance behavior tests the present peptides acting upon own receptors or through ACTH receptors in the brain may furthermore exert a psychopharmacological activity, especially a CNS depressant activity.

The peptides of the invention can be processed to customary liquid or solid pharmaceutical preparations, for example, to tablets for sublingual or oral administration, to suppositories for rectal administration or to solutions, emulsions or suspensions for oral administration but preferably for intranasal administration and/or injection purposes. The customary excipients, diluents and other auxiliaries are used for this purpose.

The peptides according to the invention are preferably administered parenterally in a daily dosage of from 0.5 μg to 0.5 mg per kg bodyweight. For intranasal administration the preferred daily dosage is from 10 μg to 50 mg per kg bodyweight, whereas the sublingual dosages are about 10 times that of the parenteral dosage.

Exceedingly valuable preparations are obtained if the present peptides are processed into a form in which they have prolonged activity, for example by incorporating the peptides into gelatin, or by converting the peptides into peptide-metal complexes. These metal complexes can be obtained in the usual manner by contacting the peptide in question with a poorly soluble metal salt, metal hydroxide or metal oxyde. The preferred metal in this respect is zinc.

The lower aliphatic acyl group used in the definition of $R_1$ of formula I is preferably acetyl, but may also be i.a. propionyl, butyryl, or 2-methyl propionyl.

By salts of the peptides of formula I are preferably meant the pharmaceutically acceptable acid addition salts but also the alkali metal salts of the peptides I are included.

The acid addition salts are obtained by reacting the present peptides with a suitable organic or inorganic acid such as HCl, $H_3PO_4$, acetic acid, maleic acid, tartaric acid or citric acid.

By amides of the peptides of formula I are to be understood those peptides of formula I in which the terminal carboxylic hydroxy group has been replaced by an amino or a mono- or dialkyl (1–4 C) substituted amino group.

Esters of the present peptides are derived from aliphatic or araliphatic alcohols with 1–18 carbon atoms; in particular the lower (1–6 C) aliphatic alcohols such as methanol, ethanol or butanol are preferred.

Preparation of the peptides of formula I can be carried out according to Ling et al., Life Science Vol. 25, pages 1773–1780 (1979).

In the following experiments the term γ-MSH is used for the peptide of formula I, in which $R_1 = H$ and $R_2 = Gly-OH$.

S.E.M., used in the examples, is: the standard error in the mean.

EXAMPLE 1

Extinction of active avoidance behavior

Male Wistar rats weighing from 120–140 g were trained on 4 consecutive days to acquire a pole-jumping avoidance response. Each day the rats were subjected to a session of 10 min. in which 10 trails were run. On the 5th day, 3 extinction sessions were run, which were separated by 2 h intervals. Immediately following the 1st extinction session rats were subcutaneously injected with 3 μg γ-MSH or placebo (0.5 ml saline).

| Mean number (± SEM) of conditioned avoidance during extinction | | | |
|---|---|---|---|
| | 0 | 2 | 4 h after injection |
| placebo | 9.0 ± 0.4 | 8.2 ± 0.9 | 6.8 ± 0.5 |
| γ-MSH | 8.3 ± 0.4 | 4.5 ± 1.3 | 2.3 ± 1.6 |

Passive avoidance behavior

Animals were testes in a step through type situation using a one trail learning procedure in which they received an unescapable shock. The latency of rats to re-enter the dark compartment during the 24 h retention trail, served as the behavioral response. The rats were injected subcutaneously with 1.5 μg γ-MSH or placebo (0.5 ml saline) 1 h before the retention trail.

| | median avoidance latency (sec) |
|---|---|
| saline | 112.5 |
| γ-MSH | 24.5 |

Acquisition of shuttle box avoidance behavior

Rats were trained to acquire a conditioned avoidance response in a shuttle box during a 30 trail single session. The conditioned stimulus (a buzzer) was followed by the unconditioned stimulus (footshock 0.15 mA) with a delay of 3 sec. The mean intertrial interval was 60 sec. The animals were treated subcutaneously with γ-MSH (2.0 μg), placebo (0.5 ml) or naloxone (80 μg) 60 min (γ-MSH) or 10 min (naloxone) before testing was started.

| Mean (± SEM) conditional avoidance responses | |
|---|---|
| placebo | 16.8 ± 0.9 |
| γ-MSH | 6.5 ± 1.2 |
| placebo | 19.7 ± 1.3 |
| naloxon | 10.8 ± 2.6 |

EXAMPLE 2

| Influence of γ-MSH on the excessive grooming response elicited by $ACTH_{1-24}$ | | |
|---|---|---|
| Treatment | | |
| s.c. | i.c.v. | grooming score (mean + SEM) |
| placebo | $ACTH_{1-24}$ | 166 ± 10 |
| γ-MSH | $ACTH_{1-24}$ | 99 ± 15 |
| placebo | placebo | 22 ± 6 |

Male Wistar rats weighing 140–160 g and equipped with a polyethylene canula in one of the lateral brain ventricles about 1 week before experimentation were treated subcutaneously with γ-MSH (100 μg) or placebo (0.5 ml saline) and after 15 min an icv injection of $ACTH_{1-24}$ (0.3 μg) or placebo (3 μl saline) was given. Immediately thereafter the rats were placed individually into glass boxes and 15 min. later the behavioral analysis was started. During a 50 min. period the observer determined every 15th s whether the rat displayed grooming. This sample procedure yields a maximum of 200 positive grooming scores.

EXAMPLE 3

Influence of γ-MSH on β-endorphin induced temperature changes is grafically shown in FIG. 1

Before and at various time intervals after icv injection core temperature of male Wistar rats weighing 150–170 g was measured with a thermistor probe which was inserted about 6 cm into the rectum of the rat and estimated to within 0.1° C. Groups of animals were treated with either β-endorphin (20 μg) or β-endorphin (20 μg)+γ-MSH (50 μg). Placebo or γ-MSH (50 μg) injected rats served as controls. The temperature changes were corrected for the mean value obtained in controls in each experiment. The data are presented as mean temperature changes (°C.) ±SEM versus time after treatment. The shaded area represent the SEM of placebo injected rats. In the graph the symbol "O" is used for β-endorphin results and the symbol "●" for the mixture of β-endorphin and γ-MSH.

EXAMPLE 4

Figure 2:
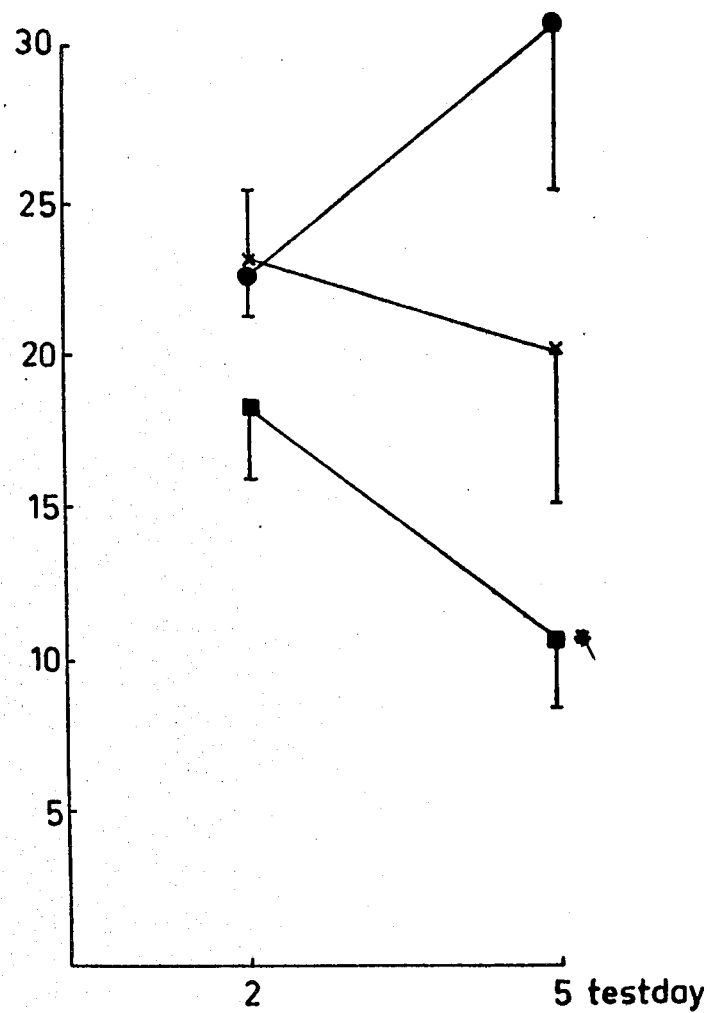

Influence of γ-MSH on intravenous heroin self-administering behavior of Male Wistar rats weighing 200–220 g is shown in FIG. 2.

The animals were allowed to self-administer heroin (0.3 mg/injection) via the intravenous route on a continuous reinforcement schedule in a 5 days, 6 hours per day, test procedure.

One hour prior to each daily experimental session animals were injected subcutaneously with 5 μg (x-x) γ-MSH or 50 μg (•—•) γ-MSH or placebo (0.5 ml saline, •—•). The mean number of self-injection (±SEM) on the 2nd and 5th testday are presented.

We claim:

1. A pharmaceutical composition, useful in counteracting the effects of narcotic analgesia in humans, containing, as active ingredient, an anti-narcotic analgetic effective amount of a peptide of the formula:

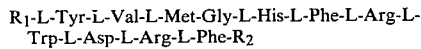

R$_1$-L-Tyr-L-Val-L-Met-Gly-L-His-L-Phe-L-Arg-L-Trp-L-Asp-L-Arg-L-Arg-L-Phe-R$_2$ in which
R$_1$ is hydrogen or a lower aliphatic acyl (1-6 C) group, and
R$_2$ represents a hydroxy group or the group —Gly—OH, or a salt, ester or amide thereof,
in admixture with the usual pharmaceutically acceptable diluents or carriers, in dosage units for parenteral administration to patients in amounts of 0.5 μg to 0.5 mg. per kg. of body weight per day; in dosage units for intranasal administration to patients in amounts of from 10 μg to 50 mg. per kg. of body weight per day; or in dosage units for sublingual or oral administration to patients in amounts from 5.0 μg to 5.0 mg. per kg. of body weight.

2. A pharmaceutical composition according to claim 1 wherein the active ingredient is a peptide of formula I, in which
R$_1$ is hydrogen and
R$_2$ represents —Gly—OH, or a salt, ester or amide thereof.

3. A method of treating patients in need of counteracting the effects of narcotic analgesia by administering to said patients an anti-narcotic analgesic in the form of a pharmaceutical composition containing, as active ingredient, a peptide of the formula:

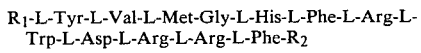

R$_1$-L-Tyr-L-Val-L-Met-Gly-L-His-L-Phe-L-Arg-L-Trp-L-Asp-L-Arg-L-Arg-L-Phe-R$_2$ in which
R$_1$ is hydrogen or a lower aliphatic acyl (1-6 C) group, and
R$_2$ represents a hydroxy group or the group —Gly—OH, or a salt, ester or amide thereof,
in admixture with the usual pharmaceutically acceptable diluents or carriers.

4. The method of treatment of claim 3 wherein the pharmaceutical composition according to claim 3 contains, as active ingredient, a peptide of formula I, in which
R$_1$ is hydrogen and
R$_2$ represents —Gly—OH, or a salt, ester or amide thereof.

5. A method of treatment according to claim 3 or claim 4 wherein the daily dosage of active ingredient,
(a) when administered parenterally, is from 0.5 μg to 0.5 mg per kg of body weight;
(b) when administered intranasally, is from 10 μg to 50 mg per kg of body weight; or
(c) when administered sublingually, is from about 5.0 μg to 5.0 mg per kg of body weight.

* * * * *